US00PP31244P2

(12) United States Plant Patent
Zhao et al.

(10) Patent No.: US PP31,244 P2
(45) Date of Patent: Dec. 17, 2019

(54) ***NELUMBO* PLANT NAMED 'ZHIJIANG QIUYUE'**

(50) Latin Name: *Nelumbo nucifera*
Varietal Denomination: Zhijiang Qiuyue

(71) Applicants: Xun Zhao, Hangzhou (CN); Yuchu Chen, Hangzhou (CN)

(72) Inventors: Xun Zhao, Hangzhou (CN); Yuchu Chen, Hangzhou (CN)

(73) Assignee: Zhejiang Renwen Landscape Architecture Co., Ltd., Hangzhou (CN)

( * ) Notice: Subject to any disclaimer, the term of this patent is extended or adjusted under 35 U.S.C. 154(b) by 0 days.

(21) Appl. No.: 16/350,037

(22) Filed: Sep. 17, 2018

(51) Int. Cl.
*A01H 5/02* (2018.01)

(52) U.S. Cl.
USPC ..... Plt./342

(58) Field of Classification Search
USPC ..... Plt./342
CPC ..... A01H 6/00; A01H 5/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Nelumbo* plant named 'Zhijiang Qiuyue', characterized by its upright plant habit; moderately vigorous growth habit; large medium green-colored leaves; freely flowering habit; and large pale yellow and green white-colored plated globose-shaped flowers that are positioned above the foliar plane on moderately strong and erect peduncles.

2 Drawing Sheets

Botanical designation: *Nelumbo nucifera*.
Cultivar denomination: 'ZHIJIANG QIUYUE'.

CROSS-REFERENCED TO CLOSELY-RELATED APPLICATIONS

Title: *Nelumbo* Plant Named 'Yanzhuang Zhaojun'
Applicants: Dongbei Yu & Yanrong Fu
Filed: Concurrently with this application

BACKGROUND OF THE INVENTION

The present invention relates to a new and distinct cultivar of *Nelumbo* plant, botanically known as *Nelumbo nucifera*, commonly referred to as Sacred or Indian Lotus, and hereinafter referred to by the name 'Zhijiang Qiuyue'.

The new *Nelumbo* plant is a product of a controlled breeding program conducted by the Inventors in Hangzhou, Zhejiang, China. The objective of the breeding program is to create new *Nelumbo* plants that have attractive and unique flower forms and flower colors.

The new *Nelumbo* plant originated from a cross-pollination in July, 2014 of *Nelumbo nucifera* 'Youyi Mudan', not patented, as the female, or seed, parent with *Nelumbo nucifera* 'Ziqi Xilai', not patented, as the male, or pollen, parent. The new *Nelumbo* plant was discovered and selected by the Inventors as a single flowering plant within the progeny of the stated open-pollination in a controlled greenhouse environment in Hangzhou, Zhejiang, China in July, 2015.

Asexual reproduction of the new *Nelumbo* plant by rhizome divisions in a controlled environment in Hangzhou, Zhejiang, China since April, 2017 has shown that the unique features of this new *Nelumbo* plant are stable and reproduced true to type in successive generations of asexual reproduction.

SUMMARY OF THE INVENTION

Plants of the new *Nelumbo* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Zhijiang Qiuyue'. These characteristics in combination distinguish 'Zhijiang Qiuyue' as a new and distinct *Nelumbo* plant:

1. Upright plant habit.
2. Moderately vigorous growth habit.
3. Large medium green-colored leaves.
4. Freely flowering habit.
5. Large pale yellow and green white-colored plated globose-shaped flowers that are positioned above the foliar plane on moderately strong and erect peduncles.

Plants of the new *Nelumbo* differ from plants of the female parent, 'Youyi Mudan', in the following characteristics:

1. Plants of the new *Nelumbo* are smaller than plants of 'Youyi Mudan'.
2. Flowers of plants of the new *Nelumbo* have pale yellow and green white-colored petals and petaloids whereas flowers of plants of 'Youyi Mudan' have light orange-colored petals and petaloids.
3. Plants of the new *Nelumbo* flower for a longer period of time than plants of 'Youyi Mudan'.

Plants of the new *Nelumbo* differ primarily from plants of the male parent, 'Ziqi Xilai' in the following characteristics:

1. Flowers of plants of the new *Nelumbo* have pale yellow and green white-colored petals and petaloids whereas petals and petaloids of flowers of plants of 'Ziqi Xilai' are red purple in color.
2. Plants of the new *Nelumbo* flower for a longer period of time than plants of 'Ziqi Xilai'.

Plants of the new *Nelumbo* differ primarily from plants of *Nelumbo nucifera* 'Yanzhuang Zhaojun', disclosed in a U.S. Plant Patent application filed concurrently, in flower color as flowers of plants of the new *Nelumbo* have pale yellow and green white-colored petals and petaloids whereas petals and petaloids of flowers of plants of 'Yanzhuang Zhaojun' are red purple and white in color.

Plants of the new *Nelumbo* can be compared to plants of *Nelumbo nucifera* 'Yudie Jinzhu', not patented. In side-by-side comparisons plants of the new *Nelumbo* differ primarily from plants of 'Yudie Jinzhu' in flower color as flowers of plants of the new *Nelumbo* have pale yellow and green white-colored petals and petaloids whereas flowers of plants of 'Yudie Jinzhu' have yellow-colored petals and petaloids.

Plants of the new *Nelumbo* can be compared to plants of *Nelumbo nucifera* 'Haojing', not patented. In side-by-side comparisons plants of the new *Nelumbo* differ primarily from plants of 'Haojing' in flower color as flowers of plants of the new *Nelumbo* have pale yellow and green white-colored petals and petaloids whereas flowers of plants of 'Haojing' have yellow green and yellow orange bi-colored petals and petaloids. In addition, plants of the new *Nelumbo* have plated globose-shaped flowers whereas plants of 'Haojing' have bowl-shaped flowers.

BRIEF DESCRIPTION OF THE PHOTOGRAPHS

The accompanying photographs illustrate the overall appearance of the new *Nelumbo* plant showing the colors as true as it is reasonably possible to obtain in colored reproductions of this type. Colors in the photographs may differ slightly from the color values cited in the detailed botanical description which accurately describe the colors of the new *Nelumbo* plant.

The photograph on the first sheet is a side perspective view of a typical plant of 'Zhijiang Qiuyue' grown in a container.

The photograph on the second sheet is a close-up view of a typical flower of 'Zhijiang Qiuyue'.

DETAILED BOTANICAL DESCRIPTION

The aforementioned photographs and following observations and measurements describe plants grown during the summer in 120-cm by 90 by 20-cm containers in an outdoor nursery in Hangzhou, Zhejiang, China and under cultural practices typical of commercial *Nelumbo* production. During the production of the plants, day temperatures ranged from 14° C. to 33° C. and night temperatures ranged from 16° C. to 28° C. Plants were one year old when the photographs and the detailed description were taken. In the following description, color references are made to The Royal Horticultural Society Colour Chart, 2007 Edition, except where general terms of ordinary dictionary significance are used.

Botanical classification: *Nelumbo nucifera* 'Zhijiang Qiuyue'.

Parentage:

- *Female, or seed, parent.*—*Nelumbo nucifera* 'Youyi Mudan', not patented.
- *Male, or pollen, parent.*—*Nelumbo nucifera* 'Ziqi Xilai', not patented.

Propagation:

- *Type.*—By rhizome divisions.
- *Time to initiate roots, summer.*—About five days at temperatures about 27° C.
- *Time to produce a rooted young plant.*—About six days at temperatures about 27° C.
- *Root description.*—Fine, fleshy; typically white to grey brown in color, actual color of the roots is dependent on water quality, fertilizer type and formulation, substrate temperature and physiological age of roots.
- *Rooting habit.*—Not freely branching, medium density.

Plant description:

- *Plant and growth habit.*—Upright plant habit; moderately vigorous growth habit and moderate growth rate.
- *Plant height (soil level to top of foliar plane).*—About 50 cm.
- *Plant height (soil level to top of floral plane).*—About 93 cm.
- *Plant diameter.*—About 140 cm by 110 cm.

Rhizome description:

- *Arrangement and habit.*—Sympodial branching habit with about ten primary branches developing per plant each with about two secondary branches.
- *Length.*—About 80 cm to 180 cm.
- *Diameter.*—About 1.5 cm to 5.7 cm.
- *Internode length.*—About 11 cm to 28 cm.
- *Texture and luster.*—Smooth, glabrous; glossy.
- *Color.*—White, close to NN155D.

Leaf description:

- *Length, fully expanded.*—About 29 cm to 38 cm.
- *Width, fully expanded.*—About 25 cm to 35 cm.
- *Shape.*—Peltate, orbicular.
- *Apex.*—Retuse.
- *Base.*—Cuneate.
- *Margin.*—Entire; undulate.
- *Venation.*—Palmate.
- *Texture and luster, upper and lower surfaces.*—Pubescent, papery; moderately glossy.
- *Color.*—Developing leaves, upper surface: Close to 144A. Developing leaves, lower surface: Close to 138C. Fully expanded leaves, upper surface: Close to 137A; venation, close to 137D. Fully expanded leaves, lower surface: Close to 138C; venation, close to 144B.
- *Petioles.*—Length: About 39 cm. Diameter: About 5 mm to 8 mm. Strength: Moderately strong. Texture and luster, upper and lower surfaces: Smooth, glabrous; moderately glossy. Color: Close to 138C.

Inflorescence description:

- *Arrangement.*—Double-type plated globose-shaped flowers developing directly from the rhizomes with numerous showy petals and petaloids; about 17 flower buds and flowers developing per plant at one time.
- *Time to flower.*—In China, plants flower from June to August; flowering continuous during this period; flowers begin opening at 05:00 hours in the morning, flowers are fully opened at about 06:30 hours and are typically closed by 09:00 hours.
- *Flower longevity.*—Flowers last about four days on the plant; flowers last about five to six days as a cut flower; flowers persistent; plants maintain good substance for about 95 days.
- *Fragrance.*—Initially, very faint and then not detectable.
- *Flower buds.*—Length: About 7.8 cm. Diameter: About 4.5 cm. Shape: Ovate. Texture and luster: Smooth, glabrous; matte. Color: Close to 145C.

*Flowers*.—Shape and arrangement: Double-type, plated globose-shaped with numerous showy petals and petaloids. Diameter: About 17.5 cm. Height: About 8 cm to 12 cm.

*Petals*.—Quantity and arrangement: About 121 arranged in numerous whorls. Length: About 10 cm. Width: About 7 cm. Shape: Obovate. Apex: Acuminate. Base: Cuneate. Margins: Entire; not undulate. Texture and luster, upper surface: Slightly rugose, glabrous; moderately glossy. Texture and luster, lower surface: Smooth, glabrous; slightly glossy. Color: When opening, upper surface: Distally, close to 3D; mid-section and towards the base, close to 157C; at the base, close to 63C. When opening, lower surface: Distally, close to 4D; mid-section and towards the base, close to 157D; at the base, close to 63C. Fully opened, upper surface: Distally, close to 3D; mid-section and towards the base, close to 157C; at the base, close to 63C; venation, close to 157C; color becoming closer to 158D with development. Fully opened, lower surface: Close to 157C; venation, close to 157D; color becoming closer to 64D with development.

*Petaloids*.—Quantity and arrangement: About 106 arranged in numerous whorls. Length: About 5.4 cm. Width: About 1.4 cm. Shape: Oblanceolate. Apex: Obtuse. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening, upper surface: Distally, close to 3D; mid-section and towards the base, close to 157C; at the base, close to 63C. When opening, lower surface: Distally, close to 4D; mid-section and towards the base, close to 157D; at the base, close to 63C. Fully opened, upper surface: Distally, close to 3D; mid-section and towards the base, close to 157C; at the base, close to 63C; venation, close to 157C; color becoming closer to 158D with development. Fully opened, lower surface: Close to 157C; venation, close to 157D; color becoming closer to 64D with development.

*Sepals*.—Quantity and arrangement: About six in a single whorl. Length: About 6.6 cm. Width: About 4.5 cm. Shape: Obovate. Apex: Acuminate. Base: Cuneate. Texture and luster, upper and lower surfaces: Smooth, glabrous; moderately glossy. Color: When opening, upper surface: Distally, close to 3D; mid-section and towards the base, close to 157C; at the base, close to 63C. When opening, lower surface: Distally, close to 4D; mid-section and towards the base, close to 157D; at the base, close to 63C. Fully opened, upper surface: Distally, close to 3D; mid-section and towards the base, close to 157C; at the base, close to 63C. Fully opened, lower surface: Close to 157C.

*Peduncles*.—Length: About 60 cm to 80 cm. Diameter: About 1.2 cm to 1.6 cm. Strength: Moderately strong. Aspect: Mostly erect. Texture and luster: Smooth, glabrous; slightly glossy. Color: Close to 144B.

*Stamens*.—Quantity per flower: About 84. Filament length: About 1.4 cm to 1.6 cm. Filament color: Close to 4C. Anther length: About 1.3 cm to 1.5 cm. Anther width: About 8 mm to 12 mm. Anther shape: Lanceolate. Anther color: Close to 6C. Pollen amount: Moderate. Pollen color: Close to 6C.

*Pistils*.—Quantity per flower: About 22. Pistil length: About 5 cm to 8 cm. Style length: About 2.4 cm. Style color: Close to 1B. Stigma diameter: About 1 mm. Stigma shape: Rounded. Stigma color: Close to 7A. Ovary color: Close to 1B.

*Fruits*.—Quantity per plant: About 15 to 30. Length: About 5 cm to 9 cm. Diameter: About 9 cm to 14 cm. Texture: Smooth, glabrous. Color: Close to 138B.

*Seeds*.—Quantity per fruit: About 9 to 16. Length: About 2.7 cm. Diameter: About 1.4 cm. Texture: Smooth, glabrous. Color: Close to N199A.

Pathogen & pest resistance: To date, plants of the new *Nelumbo* have not been observed to be resistant to pathogens or pests common to *Nelumbo* plants.

Temperature tolerance: Plants of the new *Nelumbo* have been observed to be tolerant to temperatures ranging from about −3° C. to about 37° C.

It is claimed:

1. A new and distinct *Nelumbo* plant named 'Zhijiang Qiuyue' as illustrated and described.

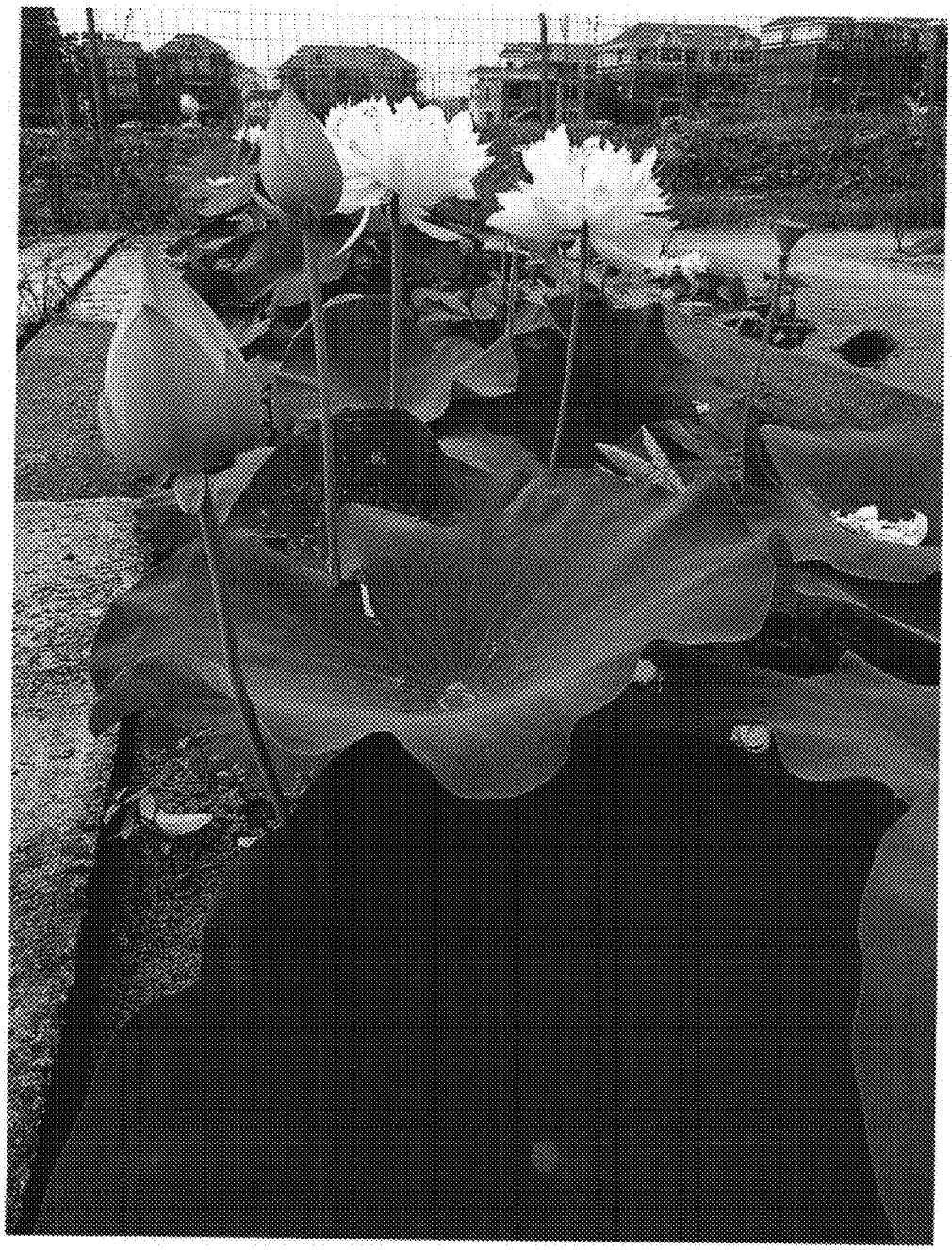

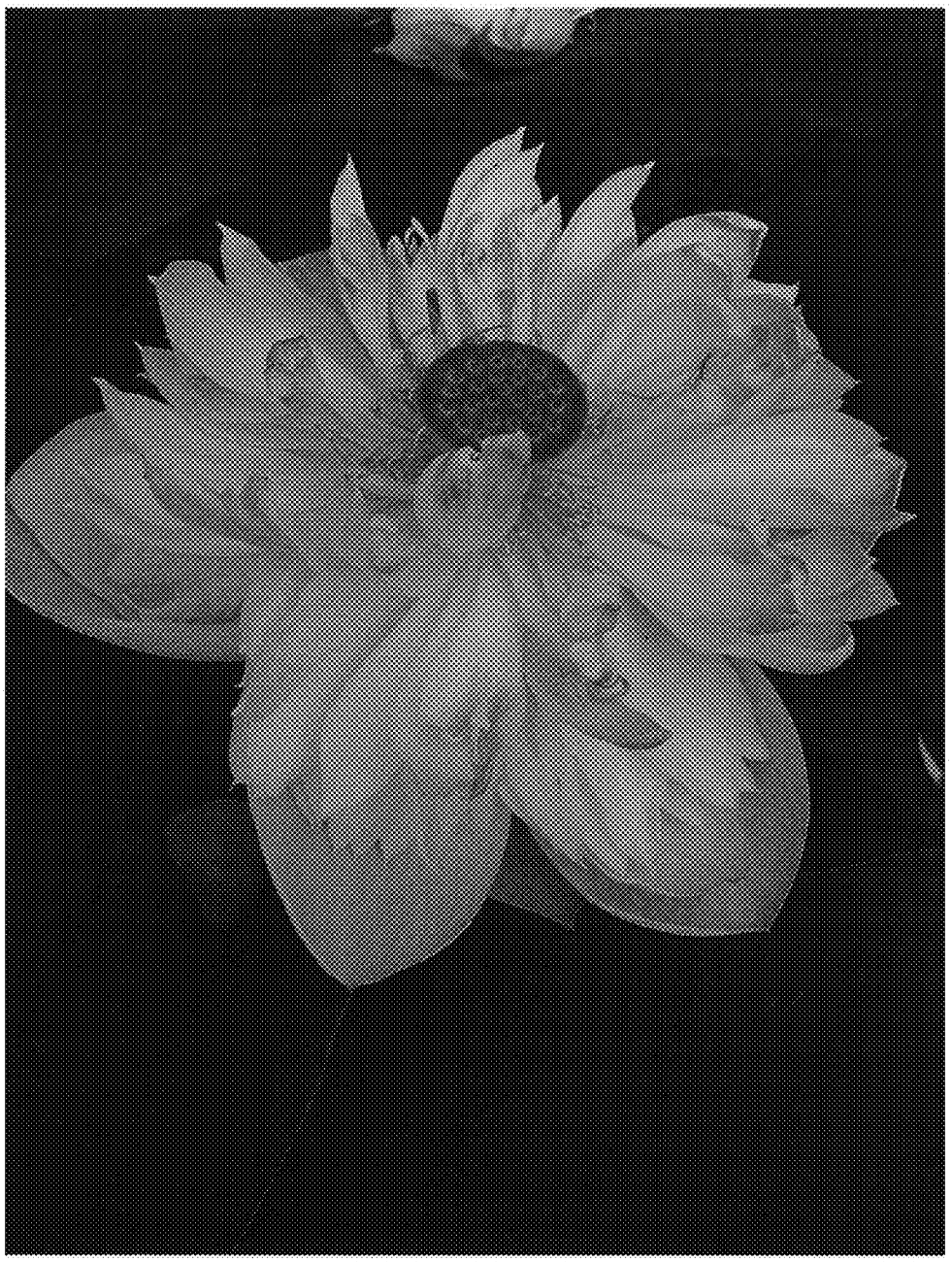

* * * * *